United States Patent
Uyama et al.

(10) Patent No.: US 12,296,040 B2
(45) Date of Patent: May 13, 2025

(54) COSMETIC OIL THICKENER AND OIL-SOLUBLE COPOLYMER

(71) Applicant: Shiseido Company, Ltd., Tokyo (JP)

(72) Inventors: Makoto Uyama, Tokyo (JP); Kazuyuki Miyazawa, Tokyo (JP); Mineo Abe, Kyoto (JP); Takuya Furuta, Kyoto (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 18/217,298

(22) Filed: Jun. 30, 2023

(65) Prior Publication Data

US 2023/0338271 A1 Oct. 26, 2023

Related U.S. Application Data

(62) Division of application No. 17/052,729, filed as application No. PCT/JP2019/017078 on Apr. 22, 2019, now abandoned.

(30) Foreign Application Priority Data

May 23, 2018 (JP) ................................ 2018-098765

(51) Int. Cl.
| | |
|---|---|
| A61K 8/81 | (2006.01) |
| A61Q 19/00 | (2006.01) |
| C08F 220/06 | (2006.01) |
| C08F 220/18 | (2006.01) |
| C08F 220/20 | (2006.01) |
| C08F 220/28 | (2006.01) |
| C08F 220/56 | (2006.01) |
| C08F 220/58 | (2006.01) |

(52) U.S. Cl.
CPC .......... *A61K 8/8152* (2013.01); *A61K 8/8111* (2013.01); *A61Q 19/00* (2013.01); *C08F 220/06* (2013.01); *C08F 220/1808* (2020.02); *C08F 220/1812* (2020.02); *C08F 220/1818* (2020.02); *C08F 220/20* (2013.01); *C08F 220/282* (2020.02); *C08F 220/287* (2020.02); *C08F 220/56* (2013.01); *C08F 220/58* (2013.01); *A61K 2800/10* (2013.01); *A61K 2800/48* (2013.01)

(58) Field of Classification Search
None
See application file for complete search history.

(56) References Cited

U.S. PATENT DOCUMENTS

| | | |
|---|---|---|
| 3,377,285 A | 4/1968 | Randles |
| 4,172,122 A | 10/1979 | Kubik et al. |
| 4,552,755 A | 11/1985 | Randen |
| 4,986,924 A | 1/1991 | Germanaud et al. |
| 2003/0118629 A1 | 6/2003 | Scholz et al. |
| 2009/0000727 A1 | 1/2009 | Kumar et al. |
| 2009/0087398 A1 | 4/2009 | Brown et al. |
| 2010/0028687 A1 | 2/2010 | Kamiya et al. |
| 2013/0047348 A1 | 2/2013 | Smith et al. |
| 2015/0119524 A1 | 4/2015 | Mitomi et al. |
| 2016/0113860 A1 | 4/2016 | Kikuchi |
| 2017/0348219 A1 | 12/2017 | Uyama et al. |

FOREIGN PATENT DOCUMENTS

| | | |
|---|---|---|
| EP | 0134483 A2 * | 3/1985 |
| EP | 0 661 964 B1 | 7/1995 |
| EP | 1 097 638 B1 | 5/2001 |
| EP | 2 630 949 B1 | 8/2013 |
| FR | 2871684 A1 | 12/2005 |
| JP | 02-110183 A | 4/1990 |
| JP | 2005-517518 A | 6/2005 |
| JP | 2014-218468 A | 11/2014 |
| JP | 2015-189961 A | 11/2015 |
| JP | 2016-210711 A | 12/2016 |
| WO | WO-03/028766 A1 | 4/2003 |
| WO | WO-2010/147412 A9 | 12/2010 |
| WO | WO-2016/098456 A1 | 6/2016 |

OTHER PUBLICATIONS

PE2E Machine Translation of FR-2871684-A1, Dec. 2005.
Written Opinion of the International Searching Authority, PCT/JP2019/017078, Jul. 2, 2019.

* cited by examiner

*Primary Examiner* — Jennifer A Berrios
(74) *Attorney, Agent, or Firm* — Foley & Lardner LLP

(57) ABSTRACT

The invention provides a novel oil thickener that can impart a thickening effect for oils used in cosmetics, and a novel oil-soluble copolymer that can be used as the thickener. The cosmetic oil thickener of the invention is an oil-soluble copolymer having a monomer unit composed of a hydrophilic monomer, a monomer unit composed of an easily-crystallizing hydrophobic monomer, and a monomer unit composed of a poorly-crystallizing hydrophobic monomer.

3 Claims, No Drawings

COSMETIC OIL THICKENER AND OIL-SOLUBLE COPOLYMER

CROSS-REFERENCE TO RELATED APPLICATIONS

This application is a Continuation of U.S. application Ser. No. 17/052,729, which is the U.S. National Stage of PCT/JP2019/017078, filed Apr. 22, 2019, which claims priority to JP 2018-098765, filed May 23, 2018.

FIELD

The present invention relates to a novel cosmetic oil thickener, and to a novel oil-soluble copolymer that can be used as the thickener.

BACKGROUND

In the field of cosmetics, it has been attempted to improve the ease of use of cosmetics by adding additives such as thickeners and gelling agents to the oils that are used.

PTL 1 discloses an oily liquid thickener for a transparent cosmetic, comprising polyamide-8, and a liquid higher fatty acid having a C12-C22 branched or unsaturated alkyl group or a liquid higher alcohol having a C12-C22 branched or unsaturated alkyl group.

PTL 2 discloses an oily thickener for a cosmetic comprising a specific siliconized polysaccharide compound and a silicone emulsifier.

PTL 3 discloses an oily gelling agent for a cosmetic that includes a copolymer composed of a specific hydrophobic monomer and a specific hydrophilic monomer.

CITATION LIST

Patent Literature

[PTL 1] Japanese Unexamined Patent Publication No. 2016-210711
[PTL 2] Japanese Unexamined Patent Publication No. 2014-218468
[PTL 3] International Patent Publication No. WO2016/098456

SUMMARY

Technical Problem

Various oils have been used in the field of cosmetics, and this has led to demand for novel oil thickeners capable of providing a thickening effect for the oils.

It is therefore a main object of the present invention to provide a novel oil thickener that can impart a thickening effect for oils used in cosmetics, and a novel oil-soluble copolymer that can be used as the thickener.

Solution to Problem

<Aspect 1>
A cosmetic oil thickener which is an oil-soluble copolymer having a monomer unit composed of a hydrophilic monomer, a monomer unit composed of an easily-crystallizing hydrophobic monomer, and a monomer unit composed of a poorly-crystallizing hydrophobic monomer.

<Aspect 2>
The thickener according to aspect 1, wherein the easily-crystallizing hydrophobic monomer is a monomer of 8 or more carbon atoms that is a solid at ordinary temperature, and the poorly-crystallizing hydrophobic monomer is a monomer of 8 or more carbon atoms that is a liquid at ordinary temperature.

<Aspect 3>
The thickener according to aspect 1 or 2, wherein the hydrophilic monomer is at least one monomer selected from among the following formula 1 and formula 2:

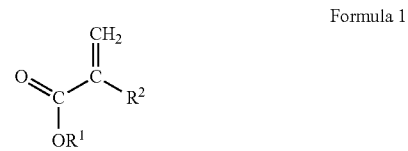

Formula 1 where,
$R^1$ is a hydrogen atom, a glyceryl group, a straight-chain or branched hydroxyalkyl group of 1 to 4 carbon atoms, or a polypropyleneglycol group represented by $-(C_3H_6O)_nH$ where n is an integer of 2 to 10, and
$R^2$ is a hydrogen atom or a methyl group,

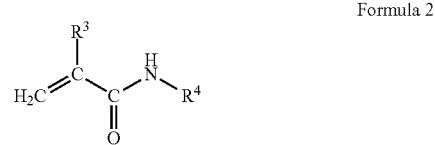

Formula 2 where,
$R^3$ is a hydrogen atom or a methyl group, and
$R^4$ is a straight-chain or branched alkyl or hydroxyalkyl group of 1 to 4 carbon atoms, or a substituent of the following formula 3.

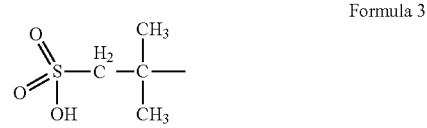

Formula 3

<Aspect 4>
The thickener according to any one of aspects 1 to 3, wherein the easily-crystallizing hydrophobic monomer is a monomer of the following formula 4:

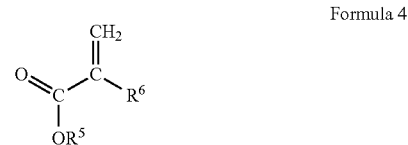

Formula 4 where,
$R^5$ is a straight-chain alkyl group of 16 to 22 carbon atoms, and
$R^6$ is a hydrogen atom or a methyl group.

<Aspect 5>
The thickener according to any one of aspects 1 to 4, wherein the poorly-crystallizing hydrophobic monomer is a monomer of the following formula 5:

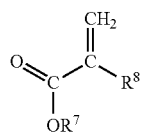

Formula 5 where,
R$^7$ is a branched alkyl group of 18 or fewer carbon atoms, or a straight-chain alkyl group of 12 or fewer carbon atoms, and
R$^8$ is a hydrogen atom or a methyl group.

<Aspect 6>
The thickener according to any one of aspects 3 to 5, wherein the monomer of formula 1 is at least one selected from among 2-hydroxyethyl (meth)acrylate, glyceryl (meth)acrylate, PPG-6 (meth)acrylate, 2-hydroxypropyl (meth)acrylate, 2-hydroxy-2-methylpropyl (meth)acrylate and (meth)acrylic acid, and the monomer of formula 2 is at least one selected from among N-(2-hydroxyethyl) (meth)acrylamide, N-isopropyl(meth)acrylamide and 2-(meth)acrylamide-2-methylpropanesulfonic acid.

<Aspect 7>
The thickener according to any one of aspects 4 to 6, wherein the monomer of formula 4 is at least one selected from among cetyl (meth)acrylate, stearyl (meth)acrylate and behenyl (meth)acrylate.

<Aspect 8>
The thickener according to any one of aspects 5 to 7, wherein the monomer of formula 5 is at least one selected from among hexyl (meth)acrylate, 2-ethylhexyl (meth)acrylate, octyl (meth)acrylate, isooctyl (meth)acrylate, decyl (meth)acrylate, isodecyl (meth)acrylate, lauryl (meth)acrylate and isostearyl (meth)acrylate.

<Aspect 9>
The thickener according to any one of aspects 1 to 8, wherein the oil-soluble copolymer contains the monomer unit of the hydrophilic monomer in a range of 30 to 50 mol %, contains the monomer unit of the easily-crystallizing hydrophobic monomer in a range of 40 to 65 mol % and contains the monomer unit of the poorly-crystallizing hydrophobic monomer in a range of 5 to mol %.

<Aspect 10>
The thickener according to any one of aspects 1 to 9, wherein the molar ratio of the monomer unit of the easily-crystallizing hydrophobic monomer and the monomer unit of the poorly-crystallizing hydrophobic monomer in the oil-soluble copolymer is 5:1 to 8:1.

<Aspect 11>
The thickener according to any one of aspects 1 to 10, wherein the weight-average molecular weight of the oil-soluble copolymer is 9000 to 80,000.

<Aspect 12>
An oil-based cosmetic containing a thickener according to any one of aspects 1 to 11 and an oil.

<Aspect 13>
An oil-soluble copolymer having:
a monomer unit composed of at least one hydrophilic monomer selected from among the following formula 1 and formula 2,
a monomer unit composed of an easily-crystallizing hydrophobic monomer of formula 4, and
a monomer unit composed of a poorly-crystallizing hydrophobic monomer of formula 5:

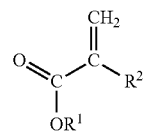

Formula 1 where,
R$^1$ is a hydrogen atom, a glyceryl group, a straight-chain or branched hydroxyalkyl group of 1 to 4 carbon atoms, or a polypropyleneglycol group represented by —(C$_3$H$_6$O)$_n$H where n is an integer of 2 to 10, and
R$^2$ is a hydrogen atom or a methyl group,

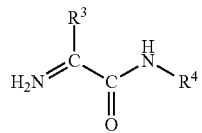

Formula 2 where,
R$^3$ is a hydrogen atom or a methyl group, and
R$^4$ is a straight-chain or branched alkyl or hydroxyalkyl group of 1 to 4 carbon atoms, or a substituent represented by the following formula 3:

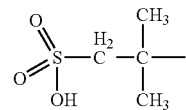

Formula 3

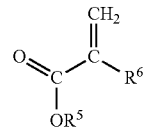

Formula 4 where,
R$^5$ is a straight-chain alkyl group of 16 to 22 carbon atoms, and
R$^6$ is a hydrogen atom or a methyl group,

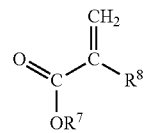

Formula 5 where,
R$^7$ is a branched alkyl group of 18 or fewer carbon atoms, or a straight-chain alkyl group of 12 or fewer carbon atoms, and
R$^8$ is a hydrogen atom or a methyl group.

Advantageous Effects of Invention

According to the invention, it is possible to provide a novel oil thickener that can impart a thickening effect for oils used in cosmetics, and a novel oil-soluble copolymer that can be used as the thickener.

DESCRIPTION OF EMBODIMENTS

Embodiments of the invention will now be explained in detail. The invention is not limited to the embodiments described below, however, and various modifications may be implemented within the scope of the gist thereof.

The cosmetic oil thickener of the invention is an oil-soluble copolymer having a monomer unit composed of a hydrophilic monomer, a monomer unit composed of an easily-crystallizing hydrophobic monomer, and a monomer unit composed of a poorly-crystallizing hydrophobic monomer.

Without being limited to any particular principle, it is believed that the principle by which the oil-soluble copolymer described above acts to impart a thickening effect by dissolution in oil is as follows.

The copolymer disclosed in PTL 3, for example, is composed of a specific hydrophobic monomer and a specific hydrophilic monomer. The hydrophobic monomer provides the function of solubility in oils, while also being easily crystallizable. Therefore, crystallization takes place between the copolymers by the hydrophobic monomer units as the copolymers approach each other, so that a network structure incorporating the oil is formed. Presumably, a similar network structure is also formed between the copolymers due to hydrogen bonding of the hydrophilic monomer units. As a result, the copolymers exhibit function as an oily gelling agent due to the two network structures. The gelatinous composition that has been gelled by the oily gelling agent, upon dilution with an oil or the like, merely separates into the gel substance and oil, thus avoiding formation of a thick composition of lower viscosity than the gelatinous composition, for example.

The oil-soluble copolymer of the invention, on the other hand, has a monomer unit composed of a poorly-crystallizing hydrophobic monomer, in addition to a monomer unit composed of a hydrophilic monomer and a monomer unit composed of an easily-crystallizing hydrophobic monomer. The poorly-crystallizing hydrophobic monomer unit inhibits crystallization of the easily-crystallizing hydrophobic monomer unit, and reduces formation of the crystallized network structure among the two network structures, thus being able to function as an oil thickener without gelation. While a copolymer composed of only a hydrophilic monomer and a poorly-crystallizing hydrophobic monomer is either poorly soluble or insoluble in oils, presumably the easily-crystallizing hydrophobic monomer unit composing the oil-soluble copolymer of the invention contributes to its solubility in oils.

The definitions of terms used for the purpose of the invention are as follows.

According to the invention, "hydrophilic monomer" means a monomer that dissolves in water to an arbitrary degree, while "hydrophobic monomer" means other monomers, i.e. monomers that are essentially not miscible with water.

The terms "easily-crystallizing hydrophobic monomer" and "poorly-crystallizing hydrophobic monomer" used for the invention refer to the monomer that crystallizes relatively easily (easily-crystallizing hydrophobic monomer) and the monomer that crystallizes relatively poorly (poorly-crystallizing hydrophobic monomer), when the two hydrophobic monomers are compared. Poorly-crystallizing hydrophobic monomers also include hydrophobic monomers that do not crystallize at all.

In other words, a hydrophobic monomer that crystallizes at high temperature after it has cooled from a molten state may be considered to be an "easily-crystallizing hydrophobic monomer", while a hydrophobic monomer that crystallizes at a lower temperature, or a hydrophobic monomer that does not crystallize, after it has cooled from a molten state, may be considered to be a "poorly-crystallizing hydrophobic monomer". The crystallization temperature of the easily-crystallizing hydrophobic monomer may be defined as 20° C. or higher, 25° C. or higher, or 30° C. or higher, for example, and the crystallization temperature of the poorly-crystallizing hydrophobic monomer may be defined as 10° C. or lower, 5° C., or lower or 0° C. or lower, for example.

The easily-crystallizing hydrophobic monomer may be a solid hydrophobic monomer that crystallizes at ordinary temperature of 8 or more, 16 or more, or 18 or more carbon atoms, and the poorly-crystallizing hydrophobic monomer may be a liquid hydrophobic monomer that crystallizes at ordinary temperature of 8 or more, 12 or more, or 16 or more carbon atoms. For this purpose, "ordinary temperature" means a temperature range of 15° C. to 25° C.

The easily-crystallizing hydrophobic monomer may be a monomer having a glass transition temperature of 10° C. or higher, 12° C. or higher, or 15° C. or higher, and 60° C. or lower, 55° C. or lower, or 50° C. or lower, for a homopolymer obtained using the monomer. The poorly-crystallizing hydrophobic monomer may be a monomer having a glass transition temperature of −90° C. or higher, −88° C. or higher, or −86° C. or higher, and 0° C. or lower, −5° C. or lower, or −10° C. or lower, for a homopolymer obtained using the monomer.

The terms "gelation" and "gelatinous", as used for the invention, can be defined as viscosity with a shear rate of near 0 s$^{-1}$ without limit, for example, static viscosity at a shear rate of 0.0001 s$^{-1}$ in a 25° C. atmosphere, and it may be defined as a range of higher than 20,000 Pa·s, 25,000 Pa·s or higher, or 30,000 Pa·s or higher. The static viscosity at a shear rate of 0.0001 s$^{-1}$ in a 25° C. atmosphere for the thickened material that has been thickened with an oil thickener of the invention, may be defined as a range of 20,000 Pa·s or lower, 15,000 Pa·s or lower, or 10,000 Pa·s or lower, and it may be defined as a range of 100 Pa·s or higher, 150 Pa·s or higher, or 200 Pa·s or higher.

The term "(meth)acrylic" according to the invention means "acrylic" or "methacrylic".

«Oil-Soluble Copolymer»

The oil-soluble copolymer of the invention has a monomer unit composed of a hydrophilic monomer, a monomer unit composed of an easily-crystallizing hydrophobic monomer, and a monomer unit composed of a poorly-crystallizing hydrophobic monomer. Such a copolymer may be either a random or block copolymer, but it is preferably random from the viewpoint of easier synthesis.

An oil-soluble copolymer may contain the monomer unit of the hydrophilic monomer at 30 mol % or greater, 32 mol %, or greater or 35 mol % or greater, and 50 mol % or less, 48 mol % or less or 45 mol % or less, from the viewpoint of the viscosity increase property; may contain the monomer unit of the easily-crystallizing hydrophobic monomer at 40 mol % or greater, 42 mol % or greater, or 45 mol % or greater, and 65 mol % or less, 63 mol % or less, 62 mol % or less, 61 mol % or less, or 60 mol % or less, from the viewpoint of solubility in oils; and may contain the monomer unit of the poorly-crystallizing hydrophobic monomer at 5 mol % or greater, 8 mol % or greater, or 9 mol % or greater, and 15 mol % or less, 13 mol % or less, or 12 mol % or less, from the viewpoint of crystallization inhibition.

In order to inhibit gelation during crystallization by the monomer unit of the easily-crystallizing hydrophobic monomer, and to more easily exhibit the viscosity increase property, the molar ratio of the monomer unit of the easily-crystallizing hydrophobic monomer and the monomer unit of the poorly-crystallizing hydrophobic monomer is preferably in the range of 5:1 to 8:1, more preferably in the range of 5:1 to 7:1 and even more preferably in the range of 5.5:1 to 6:1.

The molecular weight of the oil-soluble copolymer is not particularly restricted, and for example, it may be in the range of 9,000 to 80,000, preferably in the range of 20,000 to 50,000 and more preferably in the range of 25,000 to 40,000, as the weight-average molecular weight based on polystyrene using gel permeation chromatography.

<Hydrophilic Monomer>

Examples of hydrophilic monomers to be used include one or more monomers selected from among formula 1 and formula 2 below.

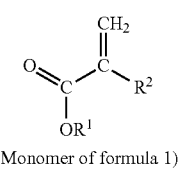

(Monomer of formula 1)

In formula 1, $R^1$ is a hydrogen atom, a glyceryl group, a straight-chain or branched hydroxyalkyl group of 1 to 4 carbon atoms, or a polypropyleneglycol group represented by $-(C_3H_6O)_nH$ wherein n is an integer of 2 to 10, and $R^2$ is a hydrogen atom or a methyl group. Examples of hydroxyalkyl groups include 2-hydroxyethyl, 2-hydroxypropyl, 2-hydroxyethyl-2-methylpropyl, 2-hydroxybutyl, 3-hydroxybutyl and 4-hydroxybutyl groups.

Specific examples of hydrophilic monomers represented by formula 1 include 2-hydroxyethyl (meth)acrylate, glyceryl (meth)acrylate, PPG-6 (meth)acrylate, 2-hydroxypropyl (meth)acrylate, 2-hydroxy-2-methylpropyl (meth)acrylate and (meth)acrylic acid, among which glyceryl (meth)acrylate, 2-hydroxyethyl (meth)acrylate and (meth)acrylic acid are preferred, and glyceryl methacrylate, 2-hydroxyethyl acrylate and acrylic acid are more preferred.

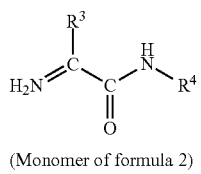

(Monomer of formula 2)

In formula 2, $R^3$ is a hydrogen atom or a methyl group, and $R^4$ is a straight-chain or branched alkyl or hydroxyalkyl group of 1 to 4 carbon atoms, or a substituent of the following formula 3.

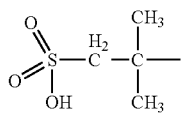

Examples of alkyl groups for $R^4$ in this formula include ethyl, propyl, isopropyl and butyl groups, and examples of hydroxyalkyl groups include 2-hydroxyethyl, 2-hydroxypropyl, 2-hydroxyethyl-2-methylpropyl, 2-hydroxybutyl, 3-hydroxybutyl and 4-hydroxybutyl groups.

Specific examples of hydrophilic monomers represented by formula 2 include N-(2-hydroxyethyl) (meth)acrylamide, N-isopropyl(meth)acrylamide and 2-(meth)acrylamide-2-methylpropanesulfonic acid. Preferred among these are N-(2-hydroxyethyl) (meth)acrylamide and N-isopropyl (meth)acrylamide, with N-(2-hydroxyethyl) (meth)acrylamide being more preferred and N-(2-hydroxyethyl)acrylamide being especially preferred.

<Easily-Crystallizing Hydrophobic Monomer>

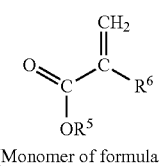

(Monomer of formula 4)

In formula 4, $R^5$ is a straight-chain alkyl group of 16 to 22 carbon atoms, and $R^6$ is a hydrogen atom or a methyl group. Examples of straight-chain alkyl groups of 16 to 22 carbon atoms include cetyl, stearyl and behenyl groups.

Such a hydrophobic monomer is an alkyl (meth)acrylate, or in other words an ester of (meth)acrylic acid and an alcohol having a straight-chain alkyl group of 16 to 22 carbon atoms. Specific examples include cetyl (meth)acrylate, stearyl (meth)acrylate, and behenyl (meth)acrylate, among which stearyl (meth)acrylate is preferred.

<Poorly-Crystallizing Hydrophobic Monomer>

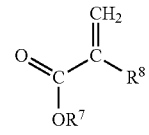

(Monomer of formula 5)

In formula 5, $R^7$ is a branched alkyl group of 18 or fewer carbon atoms, or a straight-chain alkyl group of 12 or fewer carbon atoms, and $R^8$ is a hydrogen atom or a methyl group. Straight-chain or branched alkyl groups to be used for $R^7$ include alkyl groups of 3 or more, 4 or more, 5 or more, 6 or more, 7 or more, or 8 or more carbon atoms. $R^8$ is preferably a hydrogen atom.

Specific examples of hydrophobic monomers represented by formula 5 include hexyl (meth)acrylate, 2-ethylhexyl (meth)acrylate, octyl (meth)acrylate, isooctyl (meth)acrylate, decyl (meth)acrylate, isodecyl (meth)acrylate, lauryl (meth)acrylate, and isostearyl (meth)acrylate, among which 2-ethylhexyl (meth)acrylate, octyl (meth)acrylate, lauryl (meth)acrylate, and isostearyl (meth)acrylate are preferred, octyl (meth)acrylate, lauryl (meth)acrylate, isostearyl (meth) acrylate are more preferred, and octyl (meth)acrylate and isostearyl (meth)acrylate are even more preferred.

<Optional Monomers>

The oil-soluble copolymer of the invention may also have a monomer unit composed of a monomer other than those of formulas 1, 2, 4 and 5, within a range that does not interfere with the effect of the invention. The proportion of the monomer unit may be in the range of 30 mol % or less, 20 mol % or less, 10 mol % or less, or 5 mol % or less of the total constituent monomer units. Examples of such monomers include one or more monomers selected from the group Consisting of Anionic Monomers, Cationic Monomers, Nonionic Monomers, and Other Monomers.

<Method for Producing Oil-Soluble Copolymer>

The oil-soluble copolymer of the invention can be obtained by a known polymerization method, such as charging a mixture of the hydrophilic monomer, easily-crystallizing hydrophobic monomer and poorly-crystallizing hydrophobic monomer, a polymerization solvent and a polymerization initiator into a reactor, and conducting polymerization reaction for several hours while heating to maintain a constant temperature, with no particular limitation to this method. The polymerization solvent may then be distilled off from the solution in the reactor to obtain the oil-soluble copolymer.

A copolymer can also be obtained by a living radical polymerization process. This will facilitate adjustment of the molecular weight of the copolymer, allowing a copolymer with a more narrow molecular weight distribution to be produced.

(Polymerization Solvent)

The polymerization solvent may be appropriately selected as a solvent that does not exhibit reactivity with the functional groups of the monomers. Examples include, but are not limited to, hydrocarbon-based solvents such as n-hexane, n-octane, n-decane, isodecane, cyclohexane, methylcyclohexane, toluene, xylene, ethylbenzene and cumene; alcohol-based solvents such as methanol, ethanol, n-propanol, isopropanol, n-butanol, isobutanol, n-hexanol, benzyl alcohol and cyclohexanol; hydroxyl-containing glycol ethers such as ethylene glycol, diethylene glycol, propylene glycol, dipropylene glycol, methylcellosolve, ethylcellosolve, butylcellosolve, propyleneglycol monomethyl ether, propyleneglycol monoethyl ether, propyleneglycol propyl ether, butylcarbitol, butyltriethylene glycol and methyldipropylene glycol; glycol-based solvents such as diglyme, triglyme, methylcellosolve acetate, propyleneglycol monomethyl ether acetate, dipropyleneglycol butyl ether acetate and diethyleneglycol monobutyl ether acetate; ether-based solvents such as diethyl ether, dipropyl ether, methylcyclopropyl ether, tetrahydrofuran, dioxane and anisole; ketone-based solvents such as dimethyl ketone, diethyl ketone, ethyl methyl ketone, isobutylmethyl ketone, cyclohexanone, isophorone and acetophenone; ester-based solvents such as methyl acetate, ethyl acetate, butyl acetate, propyl acetate, methyl butyrate, ethyl butyrate, caprolactone, methyl lactate and ethyl lactate; halogen-based solvents such as chloroform, dichloromethane, dichloroethane and o-dichlorobenzene; amide-based solvents such as formamide, N,N-dimethylformamide, N,N-dimethylacetamide, 2-pyrrolidone, N-methyl-2-pyrrolidone and ε-caprolactam; and dimethyl sulfoxide, sulfolane, tetramethylurea, ethylene carbonate, propylene carbonate, dimethyl carbonate, diethyl carbonate, nitromethane, acetonitrile, nitrobenzene and dioctyl phthalate.

(Polymerization Initiator)

The polymerization initiator used may be a conventionally known one, and examples include but are not particularly limited to organic peroxides and azo compounds. Specifically, these include benzoyl peroxide, dicumyl peroxide, diisopropyl peroxide, di-t-butyl peroxide, t-butyl peroxybenzoate, t-hexyl peroxybenzoate, t-butylperoxy-2-ethyl hexanoate, t-hexylperoxy-2-ethyl hexanoate, 1,1-bis(t-butylperoxy)3,3,5-trimethylcyclohexane, 2,5-dimethyl-2,5-bis(t-butylperoxy)hexyl-3,3-isopropyl hydroperoxide, t-butyl hydroperoxide, dicumyl hydroperoxide, acetyl peroxide, bis(4-t-butylcyclohexyl)peroxy dicarbonate, isobutyl peroxide, 3,3,5-trimethylhexanoyl peroxide, lauryl peroxide, 1,1-bis(t-butylperoxy)3,3,5-trimethylcyclohexane, 1,1-bis(t-hexylperoxy)3,3,5-trimethylcyclohexane, 2,2'-azobis(isobutyronitrile), 2,2'-azobis(2,4-dimethylvaleronitrile), 2,2'-azobis(4-methoxy-2,4-dimethylvaleronitrile) and dimethyl 2,2'-azobis(isobutyrate).

(Polymerization Time)

The time that the state of reflux is maintained, i.e. the polymerization time, is preferably long enough until the monomers disappear, and it may be, but is not limited to, 1 hour or longer, 2 hours or longer or 3 hours or longer, and 144 hours or shorter, 72 hours or shorter or 48 hours or shorter, for example.

(Polymerization Atmosphere)

The polymerization atmosphere is not particularly limited, and the polymerization may be in an air atmosphere, i.e. with a normal concentration of oxygen in the polymerization system, or if necessary it may be carried out in an inert gas atmosphere such as nitrogen or argon to remove the oxygen. Each of the materials used may have the impurities removed by distillation, or with active carbon or alumina, or a commercial product may be used directly. The polymerization may be conducted under shielding from light, or in a transparent container such as glass.

(Other Components Contributing to Polymerization Reaction)

Other components such as chain transfer agents may be added to the reactor as necessary for molecular weight modification of the copolymer, for example. Examples of chain transfer agents include, but are not particularly limited to, compounds with mercapto groups such as laurylmercaptane and thioglycerol; inorganic salts such as sodium hypophosphite and sodium hydrogen sulfite; and α-methylstyrene dimer. The amount of chain transfer agent used is determined as appropriate for the molecular weight range desired for the copolymer, but it is usually preferred to be in the range of 0.01 to 10 mass % with respect to the monomers.

«Usage of Oil-Soluble Copolymer»

The oil-soluble copolymer of the invention may be used for various purposes such as cosmetics, paints, inks and coating compositions, since it can be dissolved in different hydrophobic organic solvents that contain oils, thereby increasing the viscosity of such solvents. It is preferably used as an oil thickener for a cosmetic. A hydrophobic organic solvent, for this purpose, is a solvent that at least partially separates when mixed with water.

The composition that includes the oil-soluble copolymer of the invention can also be prepared as a highly transparent composition. This will allow the composition to exhibit a viscosity increase property without altering the tint of the hydrophobic organic solvent.

From the viewpoint of the viscosity increase property and stability, the amount of oil-soluble copolymer of the invention added may be 1 mass % or greater, 2 mass % or greater, or 3 mass % or greater, and 10 mass % or lower, 8 mass % or lower or 5 mass % or lower, in 100 mass % of the mixture of the copolymer and hydrophobic organic solvent.

The method of preparing the composition containing the copolymer and hydrophobic organic solvent is not particularly restricted, and for example, preferably the copolymer and hydrophobic organic solvent are mixed after both are dissolved, with heating as necessary during the dissolution and mixing.

The oil-soluble copolymer of the invention will now be described assuming its use as an oil thickener in a cosmetic, though this is not limitative on the invention.

<Cosmetic>
(Hydrophobic Organic Solvent)

When the oil-soluble copolymer of the invention is to be used as a cosmetic oil thickener, hydrophobic organic solvents may be used alone or in combination of two or more, and it is preferred to use one or more of various oils, and especially oils that are compatible with thickeners, such as hydrocarbon oils, ester oils, or higher alcohols, for example, with no limitation to these.

Hydrocarbon oils include liquid paraffin, tetraisobutane, hydrogenated polydecene, olefin oligomers, isododecane, isohexadecane, squalane and hydrogenated polyisobutene.

Ester oils include cetyl isooctanoate (cetyl 2-ethylhexanoate), triethylhexanoin, 2-ethylhexyl palmitate, neopentyl glycol dicaprate, triisostearin, diisostearyl malate, PPG-3 dipivalate, di-2-ethylhexyl succinate, 2-ethylhexyl 2-ethylhexanoate, polyglyceryl-6 octacaprylate and (caprylic/capric) triglyceride.

Higher alcohols include isostearyl alcohol and oleyl alcohol.

The total amount of hydrocarbon oils, ester oils and higher alcohols is preferably 80 mass % or greater and more preferably 85 mass % or greater in the oil.

The oil thickener of the invention can be suitably used in various cosmetics, and especially oily cosmetics or water-in-oil type emulsified cosmetics.

(Oily Cosmetics)

Examples of oily cosmetics include skin care cosmetics such as sun protection oils and beauty essences; makeup cosmetics such as lipstick, gloss, mascara and mascara foundations; skin cleansers such as makeup removers; and hair cosmetics such as hair oils and hair treatments.

(Water-In-Oil Type Emulsified Cosmetics)

Examples of water-in-oil emulsified cosmetics include skin care cosmetics such as milky lotions creams, face oils, body oils and beauty essences; makeup cosmetics such as foundations, cosmetic bases, lipstick, rouge, eye-shadow, mascara and mascara foundations; skin cleansers such as makeup removers; hair cleansers; hair cosmetics such as hair treatments and hair oils; sunscreen cosmetics; and hair dyes.

(Optional Components)

The cosmetic of the invention may also contain other components as appropriate in ranges that do not interfere with the effect of the invention. Such components include additives that can generally be added to cosmetics, examples of which are anionic surfactants, cationic surfactants, amphoteric surfactants, nonionic surfactants, humectants, water-soluble polymers, film-forming agents such as silicone modified polysaccharides, metal ion sequestering agents, lower alcohols, polyhydric alcohols, various extracts, sugars, amino acids, organic amines, polymer emulsions, chelating agents, ultraviolet absorbers, pH adjustors, skin nutrients, vitamins, drugs, quasi drugs, water-soluble drugs that are suitable for use in cosmetics, antioxidants, buffering agents, antiseptic agents, antioxidant aids, propellants, organic system powders, pigments, dyes, coloring agents, perfumes, water, acid components and alkali components. Such optional components may be added as appropriate to the oil phase, or to the aqueous phase when present.

EXAMPLES

The invention will now be described in greater detail by examples, with the understanding that they are not restrictive on the invention.

Examples 1 to 29 and Comparative Examples 1 and 2

<Synthesis of Copolymer>

In a 1 liter-volume four-necked flask equipped with a reflux condenser, thermometer, nitrogen gas inlet tube and stirrer, there were charged 250 parts by mass of ethanol, and a total of 100 parts by mass of a mixture of the monomers listed in Table 1 or Table 2 in the listed monomer molar ratios, and the mixture was heated under a nitrogen stream. When the mixture reached a state of reflux at approximately 80° C., 1 part by mass of 2,2'-azobisisobutyronitrile was added, and the reflux state was maintained for 4 hours for polymerization reaction. The ethanol solvent was then distilled off from the solution in the flask to obtain a copolymer. For Examples 12 to 18, however, the charging amounts of the ethanol and 2,2'-azobisisobutyronitrile were adjusted as appropriate for the prescribed weight-average molecular weights.

(Weight-Average Molecular Weight)

The weight-average molecular weight of the obtained copolymer was calculated from gel permeation chromatography under the following measuring conditions.

Apparatus: Prominence HPLC system (product of Shimadzu Corp.)
Column: Shodex KF-805, KF-803, KF-801 (series) (product of Showa Denko K.K.)
Mobile phase: Tetrahydrofuran
Flow rate: 1 mL/min
Detector: Differential refractometer
Temperature: 40° C.
Molecular weight reference sample: Polystyrene <Evaluation Methods>
(Evaluation of Compatibility with Oils)

The copolymer was mixed with different oils, and the compatibility of the copolymer with the oils when dissolved at 85° C. while stirring was visually observed and evaluated on the following scale, giving the results shown in Table 1. The copolymer content was adjusted to 3 mass % of the copolymer with respect to the total amount of the copolymer and oil.

A: Easily dissolved, compatible.
B: Difficult to dissolve, but compatible.
C: Slight precipitation observed.
D: Notable precipitation observed.
E: Completely incompatible.

(Evaluation of Viscosity Increase Property)

The copolymer was mixed with different oils, and each mixture was dissolved at 85° C. while stirring and then cooled to room temperature to prepare a sample. The viscosity increase property was evaluated using an MCR302 rheometer by Anton Paar, under conditions of 25° C., 1 atmosphere, on the following scale, based on the viscosity with a shear rate of near 0 $s^{-1}$ without limit, i.e. a shear rate of 0.0001 $s^{-1}$. The results are shown in Table 1. The copolymer content was adjusted to 3 mass % of the copolymer with respect to the total amount of the copolymer and oil.

A: ≥2000 Pa·s, ≤20,000 Pa·s
B: ≥1000 Pa·s, <2000 Pa·s
C: ≥100 Pa·s, <1000 Pa·s
D: ≥1 Pa·s, <100 Pa·s
E: >20,000 Pa·s (gelled)

(Transparency Evaluation)

The copolymer was mixed with different oils, and each mixture was dissolved at 85° C. while stirring and then cooled to room temperature to prepare a sample. The transparency of the sample was visually observed and evaluated on the following scale, giving the results shown in Table 1. The copolymer content was adjusted to 3 mass % of the copolymer with respect to the total amount of the copolymer and oil.

A: Excellent transparency exhibited.
B: Satisfactory transparency exhibited.
C: Slight turbidity exhibited.
D: Notable opacity.
E: Opaque.

TABLE 1

| | | Example | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Monomer (mol %) | GLM | 40 | 40 | 40 | 40 | 40 | 40 | 40 | 40 | 40 | 40 | 40 | 40 |
| | SA | 52 | 51 | 50 | 52 | 51 | 50 | 51 | 51 | 52 | 51 | 50 | 51 |
| | BEA | — | — | — | — | — | — | — | — | — | — | — | — |
| | 2EHA | 8 | 9 | 10 | — | — | — | — | — | — | — | — | — |
| | LMA | — | — | — | 8 | 9 | 10 | 9 | 9 | — | — | — | — |
| | ISA | — | — | — | — | — | — | — | — | 8 | 9 | 10 | 9 |
| | NOA | — | — | — | — | — | — | — | — | — | — | — | — |
| Weight-average molecular weight | | 55400 | 50,000 | 44100 | 75200 | 75200 | 77900 | 30900 | 34800 | 59200 | 51200 | 48900 | 9300 |
| HPD | Compatibility | B | C | D | B | B | B | A | A | B | B | B | A |
| | Viscosity increase property | A | A | B | A | A | B | C | C | A | A | B | A |
| | Transparency | E | D | C | C | C | C | C | C | B | B | B | B |
| CIO | Compatibility | B | B | C | B | B | B | A | A | B | B | B | A |
| | Viscosity increase property | B | B | B | C | C | C | D | D | A | A | B | A |
| | Transparency | E | D | C | C | C | D | C | C | B | B | B | B |

| | | Example | | | | | | | | | Comp. Ex. | |
|---|---|---|---|---|---|---|---|---|---|---|---|---|
| | | 13 | 14 | 15 | 16 | 17 | 18 | 19 | 20 | 21 | 1 | 2 |
| Monomer (mol %) | GLM | 40 | 40 | 40 | 40 | 40 | 40 | 40 | 40 | 40 | 40 | 40 |
| | SA | 51 | 51 | 51 | 51 | 51 | 51 | 51 | 51 | 51 | — | — |
| | BEA | — | — | — | — | — | — | — | — | — | 60 | — |
| | 2EHA | — | — | — | — | — | — | — | — | — | — | — |
| | LMA | — | — | — | — | — | — | — | — | — | — | — |
| | ISA | 9 | 9 | 9 | 9 | 9 | 9 | — | — | — | — | 60 |
| | NOA | — | — | — | — | — | — | 9 | 9 | 9 | — | — |
| Weight-average molecular weight | | 16300 | 23,000 | 34200 | 39500 | 43200 | 60500 | 19700 | 41800 | 57900 | 29300 | 23500 |
| HPD | Compatibility | A | A | A | A | B | D | A | A | B | A | E |
| | Viscosity increase property | A | A | A | A | A | A | A | A | A | E | — |
| | Transparency | B | B | B | B | B | B | B | B | B | E | — |
| CIO | Compatibility | A | A | A | A | A | B | A | A | B | A | E |
| | Viscosity increase property | A | A | A | A | A | A | A | A | A | E | — |
| | Transparency | B | B | B | B | B | B | B | B | B | E | — |

GLM: Glyceryl methacrylate of hydrophilic monomer (melting point: −40° C., homopolymer glass transition temperature: 55° C.).
SA: Stearyl acrylate of easily-crystallizing hydrophobic monomer (melting point: 28° C., homopolymer glass transition temperature: 35° C.).
BEA: Behenyl acrylate of easily-crystallizing hydrophobic monomer (melting point: 46° C., homopolymer glass transition temperature: 50° C.).
2EHA: 2-Ethylhexyl acrylate of poorly-crystallizing hydrophobic monomer (melting point: −90° C., homopolymer glass transition temperature: −85° C.).
LMA: Lauryl methacrylate of poorly-crystallizing hydrophobic monomer (melting point: −23° C., homopolymer glass transition temperature: −65° C.).
ISA: Isostearyl acrylate of poorly-crystallizing hydrophobic monomer (melting point: <-50° C., homopolymer glass transition temperature: −18° C.).
NOA: n-Octyl acrylate of poorly-crystallizing hydrophobic monomer (melting point: <-50° C., homopolymer glass transition temperature: −65° C.).
HPD: Hydrogenated polydecene of oil. Static viscosity at 25° C.: 0.03 Pa · s.
CIO: Cetyl isooctanoate of oil. Static viscosity at 25° C.: 0.01 Pa · s.

TABLE 2

| | | Example | | | | | | | | |
|---|---|---|---|---|---|---|---|---|---|---|
| | | 15 | 22 | 23 | 24 | 25 | 26 | 27 | 28 | 29 |
| Monomer (mol %) | GLM | 40 | — | — | — | — | — | — | — | — |
| | HEAA | — | 40 | — | — | — | — | — | — | — |
| | HEA | — | — | 40 | — | — | — | — | — | — |
| | Aa | — | — | — | 40 | — | — | — | — | — |

TABLE 2-continued

| | Example | | | | | | | | |
|---|---|---|---|---|---|---|---|---|---|
| | 15 | 22 | 23 | 24 | 25 | 26 | 27 | 28 | 29 |
| HBMA | — | — | — | — | 40 | — | — | — | — |
| NIPAM | — | — | — | — | — | 40 | — | — | — |
| HPMA | — | — | — | — | — | — | 40 | — | — |
| HEMA | — | — | — | — | — | — | — | 40 | — |
| AP-400 | — | — | — | — | — | — | — | — | 40 |
| SA | 51 | 51 | 51 | 51 | 51 | 51 | 51 | 51 | 51 |
| ISA | 9 | 9 | 9 | 9 | 9 | 9 | 9 | 9 | 9 |
| Weight-average molecular weight | 34200 | 30500 | 27,000 | 33,000 | 37500 | 36700 | 33900 | 38500 | 29300 |
| HPD Compatibility | A | A | A | A | D | A | D | A | A |
| Viscosity increase property | A | A | A | A | C | B | C | B | C |
| Transparency | B | B | B | B | C | C | C | C | C |

GLM: Glyceryl methacrylate of hydrophilic monomer.
HEAA: 2-Hydroxyethylacrylamide of hydrophilic monomer.
HEA: 2-Hydroxyethyl acrylate of hydrophilic monomer.
Aa: Acrylic acid of hydrophilic monomer
HBMA: 2-Hydroxy-2-methylpropyl methacrylate of hydrophilic monomer.
NIPAM: N-Isopropylacrylamide of hydrophilic monomer.
HPMA: 2-Hydroxypropyl methacrylate of hydrophilic monomer.
HEMA: 2-Hydroxyethyl methacrylate of hydrophilic monomer.
AP-400: PPG-6 acrylate of hydrophilic monomer.
SA: Stearyl acrylate of easily-crystallizing hydrophobic monomer
ISA: Isostearyl acrylate of poorly-crystallizing hydrophobic monomer
HPD: Hydrogenated polydecene of oil.

<Results>

As clearly seen from Table 1, with the composition of Comparative Example 1 which used a copolymer that did not include a monomer unit composed of a poorly-crystallizing hydrophobic monomer, the copolymer was compatible with oils but the composition itself gelled. With the composition of Comparative Example 2 which used a copolymer that did not include a monomer unit composed of an easily-crystallizing hydrophobic monomer, the copolymer was not compatible with oils. With the compositions of Examples 1 to 21 which used copolymers of the invention that included both monomer units, it was confirmed that the copolymers were compatible with oils, and were able to increase viscosity without gelling with at least one of the oils.

Upon comparing Examples 1 to 3 which used 2-ethylhexyl acrylate, Examples 4 to 6 which used lauryl methacrylate, Examples 9 to 11 which used isostearyl acrylate and Examples 19 to 21 which used n-octyl acrylate as the poorly-crystallizing hydrophobic monomer, it was found that using lauryl methacrylate, isostearyl acrylate or n-octyl acrylate further improved performance including transparency.

As clearly seen from Table 2, it was confirmed that the copolymers of the invention were able to increase viscosity without gelling of oils, even when using a hydrophilic monomer other than glyceryl methacrylate.

Upon comparing Example 25 which used 2-hydroxy-2-methylpropyl methacrylate and Example 27 which used 2-hydroxypropyl methacrylate, with Example 26 which used N-isopropylacrylamide and Example 28 which used 2-hydroxyethyl methacrylate as the hydrophilic monomer, it was found that Examples 26 and 28 had further improved compatibility and viscosity increase properties. With Example 15 which used glyceryl methacrylate, Example 22 which used 2-hydroxyethylacrylamide, Example 23 which used 2-hydroxyethyl acrylate and Example 24 which used acrylic acid, it was found that the compatibility, viscosity increase properties and transparency were further improved.

The invention claimed is:

1. A cosmetic containing an oil thickener, and at least one oil which is selected from the group consisting of a hydrocarbon oil, an ester oil, and a higher alcohol, wherein
the oil thickener is an oil-soluble copolymer having a monomer unit composed of a hydrophilic monomer, a monomer unit composed of an easily-crystallizing hydrophobic monomer, and a monomer unit composed of a poorly-crystallizing hydrophobic monomer,
the oil-soluble copolymer contains the monomer unit of the hydrophilic monomer in a range of 30 to 50 mol %, contains the monomer unit of the easily-crystallizing hydrophobic monomer in a range of 40 to 65 mol % and contains the monomer unit of the poorly-crystallizing hydrophobic monomer in a range of 5 to 15 mol %,
the hydrophilic monomer is at least one selected from among 2-hydroxyethyl (meth)acrylate, glyceryl (meth)acrylate, PPG-6 (meth)acrylate, 2-hydroxypropyl (meth)acrylate, 2-hydroxy-2-methylpropyl (meth)acrylate, (meth)acrylic acid, N-(2-hydroxyethyl) (meth)acrylamide, N-isopropyl(meth)acrylamide, and 2-(meth)acrylamide-2-methylpropanesulfonic acid,
the easily-crystallizing hydrophobic monomer is at least one selected from among cetyl (meth)acrylate, stearyl (meth)acrylate and behenyl (meth)acrylate,
the poorly-crystallizing hydrophobic monomer is at least one selected from among hexyl (meth)acrylate, 2-ethylhexyl (meth)acrylate, octyl (meth)acrylate, isooctyl (meth)acrylate, decyl (meth)acrylate, isodecyl (meth)acrylate, lauryl (meth)acrylate and isostearyl (meth)acrylate,
the molar ratio of the monomer unit of the easily-crystallizing hydrophobic monomer and the monomer unit of the poorly-crystallizing hydrophobic monomer in the oil-soluble copolymer is 5.5:1 to 8:1,
the amount of the oil thickener is 3 mass % or greater, in 100 mass % of a mixture of the oil thickener and the at least one oil,
the cosmetic exhibits a static viscosity of between 100 Pa·s and 20,000 Pa·s under conditions of a shear rate of 0.0001 s$^{-1}$ and 25° C. atmosphere and wherein the copolymer thickens the at least one oil without gelation.

2. The cosmetic according to claim 1, wherein the weight-average molecular weight of the oil-soluble copolymer is 9000 to 80,000.

3. The cosmetic according to claim 1, wherein the oil-soluble copolymer contains the monomer unit of the hydrophilic monomer in a range of 30 to 45 mol %, contains the monomer unit of the easily-crystallizing hydrophobic monomer in a range of 50 to 65 mol % and contains the monomer unit of the poorly-crystallizing hydrophobic monomer in a range of 5 to 15 mol %.

* * * * *